(12) United States Patent
Zeng et al.

(10) Patent No.: US 10,188,811 B2
(45) Date of Patent: Jan. 29, 2019

(54) NASAL SPRAY DEVICE

(71) Applicants: IVAX PHARMACEUTICALS IRELAND, Waterford (IE); TEVA BRANDED PHARMACEUTICAL PRODUCTS R&D, INC., Horsham, PA (US)

(72) Inventors: Xian-Ming Zeng, Miami, FL (US); Declan Walsh, Co. Kilkenny (IE); Jade Ching-Ying Ly, Miami, FL (US); Armando Morales, Miami, FL (US)

(73) Assignees: TEVA BRANDED PHARMACEUTICAL PRODUCTS R&D, INC., Horsham, PA (US); IVAX PHARMACEUTICALS IRELAND, Waterford (IE)

( * ) Notice: Subject to any disclaimer, the term of this patent is extended or adjusted under 35 U.S.C. 154(b) by 0 days.

(21) Appl. No.: 14/865,823

(22) Filed: Sep. 25, 2015

(65) Prior Publication Data

US 2016/0082204 A1 Mar. 24, 2016

Related U.S. Application Data

(63) Continuation of application No. 13/271,940, filed on Oct. 12, 2011, now abandoned.

(Continued)

(51) Int. Cl.
*A61M 15/08* (2006.01)
*B65D 83/54* (2006.01)
(Continued)

(52) U.S. Cl.
CPC ......... *A61M 15/009* (2013.01); *A61K 9/0043* (2013.01); *A61K 31/57* (2013.01); *A61M 15/08* (2013.01); *B65D 83/54* (2013.01)

(58) Field of Classification Search
CPC ..... A61M 15/009; A61M 15/08; A61K 31/57; A61K 9/0043; B65D 83/54
See application file for complete search history.

(56) References Cited

U.S. PATENT DOCUMENTS

| 5,116,311 A | 5/1992 | Lofstedt |
|---|---|---|
| 7,055,541 B2 | 3/2006 | Seifert et al. |

(Continued)

FOREIGN PATENT DOCUMENTS

| EP | 412524 A1 | 2/1991 |
|---|---|---|
| GB | 2367011 A | 3/2002 |

(Continued)

OTHER PUBLICATIONS

Intellectual Property Office of Singapore Written Opinion of counterpart Singapore Patent Application No. 201302792-5, dated Jan. 10, 2014.

(Continued)

*Primary Examiner* — Timothy Stanis
(74) *Attorney, Agent, or Firm* — Morgan, Lewis & Bockius LLP

(57) ABSTRACT

A nasal spray device for the delivery of a pharmaceutical formulation to the nasal cavity in metered doses. The device includes: a pressurised aerosol canister including a vial containing a pharmaceutical formulation including an active ingredient, a propellant and, optionally, a co-solvent, the aerosol canister further including a metering valve having a valve stem; and an actuator for the aerosol canister, the actuator including a stem block having a receptacle into which the valve stem of metering valve of the aerosol canister is received and axially located and being displaceable relative to the vial of the aerosol canister to actuate the metering valve of the aerosol canister, a sump extending below the receptacle, the stem block further defining a discharge orifice for the pharmaceutical formulation and a (Continued)

transfer channel through which a dispensed dose of the pharmaceutical formulation is able to pass from the sump to the discharge orifice.

30 Claims, 4 Drawing Sheets

Related U.S. Application Data

(60) Provisional application No. 61/392,223, filed on Oct. 12, 2010.

(51) Int. Cl.
*A61M 15/00* (2006.01)
*A61K 9/00* (2006.01)
*A61K 31/57* (2006.01)

(56) References Cited

U.S. PATENT DOCUMENTS

| | | |
|---|---|---|
| 2003/0178022 A1* | 9/2003 | Davies ............... A61K 9/008 128/200.23 |
| 2005/0220717 A1 | 10/2005 | Wu et al. |
| 2006/0107949 A1 | 5/2006 | Davies et al. |
| 2007/0175469 A1 | 8/2007 | Rohrschneider et al. |
| 2008/0163874 A1 | 7/2008 | Djupesland |
| 2008/0203193 A1 | 8/2008 | Kakade |
| 2009/0050158 A1 | 2/2009 | Wassenaar et al. |
| 2009/0159081 A1 | 6/2009 | Stadelhofer |
| 2010/0218760 A1 | 9/2010 | Anderson et al. |

FOREIGN PATENT DOCUMENTS

| | | |
|---|---|---|
| WO | WO 92/06675 | 4/1992 |
| WO | WO 99/47195 | 9/1999 |
| WO | WO 00/78286 A1 | 12/2000 |
| WO | WO 0158508 A2 | 8/2001 |

OTHER PUBLICATIONS

Newman, S.P., et al. Principles of Metered-Dose Inhaler Design, *Respir Care*, Sep. 1, 2005, vol. 50, No. 9, pp. 1177-1190.
International Preliminary Report of Patentability corresponding to International Application No. PCT/EP2011/005118, dated Apr. 16, 2013.
Guo, C. et al., Assessment of the influence factors on in vitro testing of nasal sprays using Box-Behnken experimental design, European Journal of Pharmaceutical Sciences, Elsevier, Amsterdam, NL, vol. 35, No. 5, Dec. 18, 2008, pp. 417-426.
Gabrio, B. J., Stein, S. W., Velasquez, D. J., A new method to evaluate plume characteristics of hydrofluoroalkane and chlorofluorocarbon metered dose inhalers, International Journal of Pharmaceutics, vol. 186, No. 1, Sep. 10, 1999, pp. 3-12.
Changning, Guo et al., Evaluation of Impaction Force of Nasal Sprays and Metered-Dose Inhalers Using the Texture Analyser, Dec. 18, 2008, J of Pharmaeceutrical Scienses, vol. 98, No. 8, 2799-2806.
European Patent Office Communication, "Extended European Search Report," dated Jun. 24, 2015, corresponding to Application No. 15164095.0-1662, 8 pages.

* cited by examiner

NASAL SPRAY DEVICE

CROSS-REFERENCE TO RELATED APPLICATION

This patent application is a continuation patent application of U.S. Non-Provisional patent application Ser. No. 13/271,940, filed Oct. 12, 2011, which claims priority to U.S. Provisional Patent Application No. 61/392,223, filed Oct. 12, 2010, each of which is incorporated by reference herein in its entirety.

FIELD OF THE INVENTION

This invention relates to a nasal spray device and particularly to a nasal spray device for the delivery of a pharmaceutical formulation to the nasal cavity in metered doses.

BACKGROUND OF THE INVENTION

Nasal spray devices for the delivery of medicament to the nasal cavity, particularly the nasal mucosa, can be useful for the prophylaxis and/or treatment of certain diseases and disorders of the nasal cavity. Such devices are also capable of delivering medicament to the systemic circulation via the turbinates and lymphoid tissues located at the back of the nasal cavity and to the central nervous system via the olfactory region at the top of the nasal cavity.

Nasal spray devices include unit-dose (single use) devices having syringe-like mechanisms and metered-dose devices intended for multiple usage cycles. Unit dose devices are appropriate for delivering certain medicaments such as vaccines, whereas metered-dose devices are more suited to long-term dosage regimes, for example for the treatment of rhinitis. A known metered-dose device comprises a vial containing an aqueous suspension of a suitable medicament. The vial is provided with a manually operated pump adapted to atomise metered doses of the medicament formulation for delivery to the nasal cavity. Examples of this type of nasal spray device include FLIXONASE® (fluticasone propionate, GSK), NASACORT AQ® (triamcinolone acetoinide, Sanofi-Aventis) and NASONEX® (mometasone furoate monohydrate, Schering-Plough).

Although nasal spray devices having manually operated pumps have achieved some success in the marketplace, they have a number of drawbacks. For example, manually operated pumps have a relatively large actuation force which may, for some users, such as the very young and the elderly, be difficult to achieve on a repeatable basis. Moreover, variations in the applied actuation force can lead to some users receiving medicament doses with less than optimal spray characteristics.

To address the problems associated with these known metered-dose nasal spray devices, it may be contemplated to replace the manually operated pump with a pressurised aerosol canister. A typical aerosol canister comprises a cylindrical vial containing the medicament. The medicament is typically an active ingredient together with a suitable propellant. The medicament may be in the form of a solution or a suspension in the propellant and excipients may be added to facilitate dissolution of the active ingredient (e.g. co-solvents) or to stabilise the suspension (e.g. surfactants). The vial is provided with a metering valve having an axially extending valve stem. Displacement of the valve stem relative to the vial causes the dispensation of a metered dose of the medicament formulation as an aerosol. Compared to manually operated pumps, pressurised aerosol canisters require low actuation forces and provide consistent aerosol characteristics.

However, whereas pressurised metered dose inhalers (MDIs) have found broad market acceptance in devices intended for the pulmonary administration of medicaments by inhalation via the mouth into the lungs, MDIs have not found applications in nasal spray devices. It has generally been considered that nasal spray formulations cannot tolerate the excipients found in pMDI formulations. In particular, the high levels of co-solvents, such as ethanol, found in solution formulations are poorly tolerated by patients on account of the unpleasant sensation which they produce in the nasal cavity on administration. By way of an example, WO 92/06675 describes a medicament formulation for a pMDI comprising beclomethasone dipropionate, a co-solvent and an HFA propellant. The disclosure is principally directed to administration of the formulation by inhalation into the lungs via the mouth. There is a mention that the formulation may be administered nasally; however, there is no disclosure of how this method of administration can be achieved and there is no consideration of the problem of poor patient tolerability for nasal applications.

SUMMARY OF THE INVENTION

Accordingly, the present invention provides a nasal spray device for the delivery of a pharmaceutical formulation to the nasal cavity in metered doses, the device comprising:

a pressurised aerosol canister including a vial containing a pharmaceutical formulation comprising an active ingredient, a propellant and, optionally, a co-solvent, the aerosol canister further including a metering valve having a valve stem; and an actuator for the aerosol canister, the actuator including a stem block having a receptacle into which the valve stem of metering valve of the aerosol canister is received and axially located and being displaceable relative to the vial of the aerosol canister to actuate the metering valve of the aerosol canister, a sump extending below the receptacle, the stem block further defining a discharge orifice for the pharmaceutical formulation and a transfer channel through which a dispensed dose of the pharmaceutical formulation is able to pass from the sump to the discharge orifice, wherein the actuator further comprises a delivery outlet for the aerosol plume, the discharge orifice being arranged to direct the aerosol plume through the delivery outlet, and wherein the device is adapted to produce an aerosol plume for a dispensed dose having a spray force value no greater than 40 mN measured at a distance of 30 mm from the discharge orifice.

In an embodiment according to the present invention, wherein the formulation is a solution formulation. In an alternative embodiment according to the present invention, wherein the formulation is a suspension formulation. Accordingly, use of the term formulation encompasses is both solution and suspension formulations.

The present invention also provides the use of the nasal spray device for the delivery of a pharmaceutical formulation (solution or suspension) to the nasal cavity in metered doses.

It has now surprisingly been found that even formulations containing high levels of co-solvent are well tolerated in a nasal spray formulation, provided the nasal spray device used to deliver the formulation to the nasal cavity is adapted to provide a so-called "soft spray". The nasal spray device having the propellant-based formulation described hereinbelow provides the advantages of a metered dose pressurised aerosol canister without suffering from the disadvantage of poor patient tolerability.

BRIEF DESCRIPTION OF THE DRAWINGS

The present invention will now be described with reference to the accompanying drawings, in which.

DETAILED DESCRIPTION OF THE DRAWINGS

Figure 1:
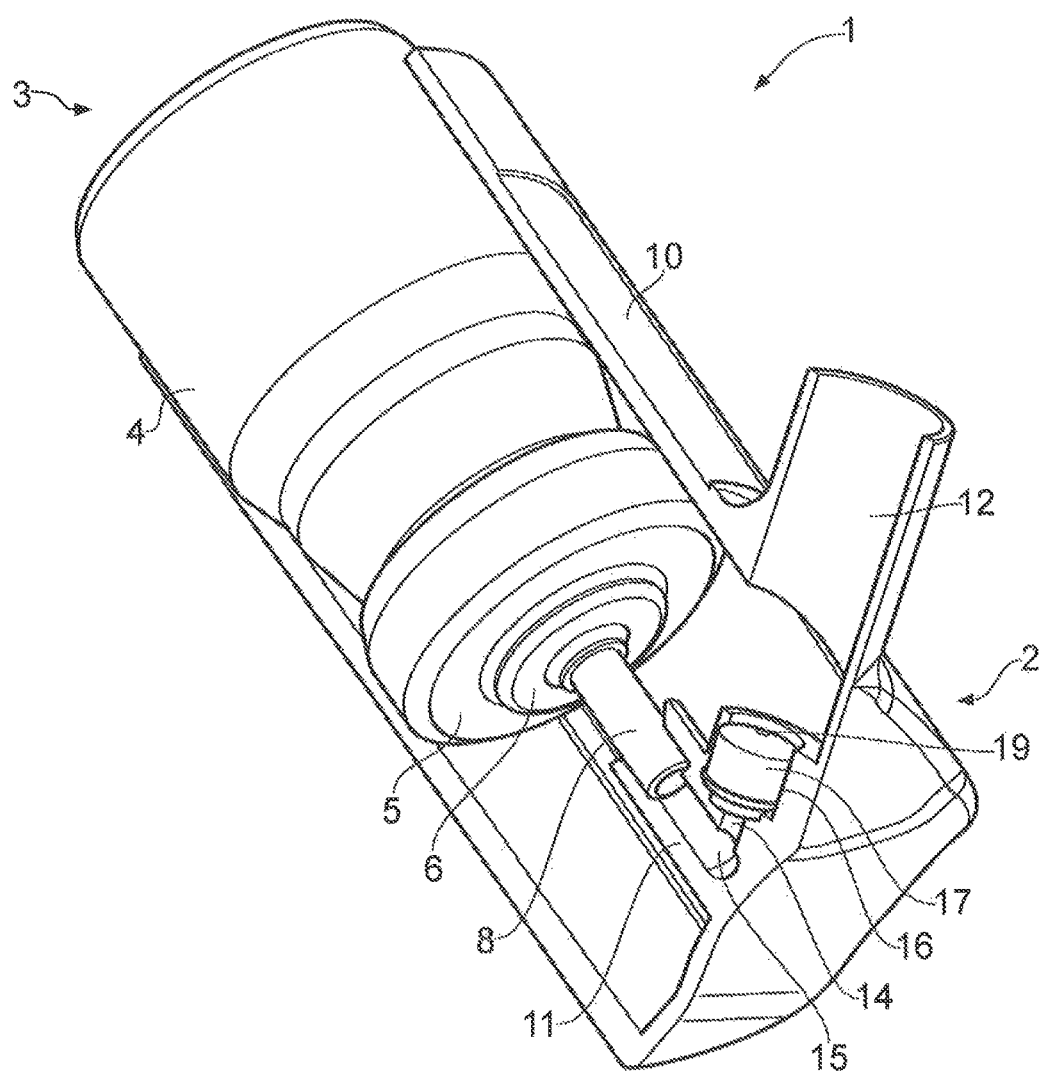
FIG. 1 shows a cut-away perspective schematic view of a nasal spray device according to the present invention.

The nasal spray device of the present invention contains an active ingredient. The pharmaceutical formulation of the present invention comprises an active ingredient and a propellant. In principle, any pharmaceutically active ingredient which is soluble or suspended in the formulation and acts via the cavity, such as the nasal mucosa, may be used in the present invention. The active ingredient is generally present in the formulation of the invention in a therapeutically effective amount, i.e. an amount such that metered volumes of the medicament administered to the patient contains an amount of drug effective to exert the intended therapeutic action. Non-limiting examples of the active ingredient which may be used in the formulation of the present invention are as follows:

(i) Steroids, such as alcometasone, beclomethasone, betamethasone, budesonide, ciclesonide, clobetasol, deflazacort, diflucortolone, desoxymethasone, dexamethasone, fludrocortisone, flunisolide, fluocinolone, fluometholone, fluticasone, hydrocortisone, mometasone furoate, nandrolone decanoate, neomycin sulfate, rimexolone, methylprednisolone, prednisolone and triamcinolone acetonide. The steroid is preferably beclomethasone dipropionate, budesonide, fluticasone propionate or mometasone furoate. Beclomethasone dipropionate (also termed beclometasone dipropionate (INN) or (8S,9R,10S,11S,13S,14S,16S,17R)-9-chloro-11-hydroxy-10,13,16-trimethyl-3-oxo-17-[2-(propionyloxy)acetyl]-6,7,8,9,10,11,12,13,14,15,16,17-dodecahydro-3H-cyclopenta[a]phen-anthren-17-yl propionate (IUPAC)) is particularly preferred.

(ii) Short- and long-acting $\beta_2$-adrenergic agonists. Long-acting $\beta_2$-agonists (LABAs) include formoterol, salmeterol and salts thereof, such as formoterol fumarate and salmeterol xinafoate. Short-acting $\beta_2$-agonists include salbutamol, terbutaline and salts thereof such as salbutamol sulfate.

(iii) Anticholinergics, such as muscarinic receptor antagonists, e.g. dexpyrronium bromide, glycopyrronium bromide, ipratropium bromide, oxitropium bromide and tiotropium bromide.

(iv) Other drugs, such as ACE inhibitors, acetylcholinesterase inhibitors, alpha-blockers, analgesics, e.g. opioids, angiotension II receptor blockers, antiarrhythmics, antibiotics, anti-cancer agents, anti-clotting agents, antidepressants, anti-emetics, antihistamines, anti-fungal drugs, anti-inflammatory agents, antipsychotics, anti-viral agents, bisphosphonates, calcium channel blockers, diuretics, dopamine agonists, hormonal drugs, hypoglycaemics, immunoglobulins, leukotriene receptor antagonists, local anaesthetics, mucolytic agents, narcotic agonists and opiate antidotes, nitrates, NMDA receptor antagonists, nucleic acids, phosphodiesterase 4 (PDE4) inhibitors, polypeptides, potassium channel modulators, serotonin agonists, serotonin antagonists, smoking cessation drugs and sympathomimetic drugs.

A therapeutically effective amount of the active ingredient needs to be delivered and this amount will vary depending on the nature of the active ingredient. A typical range is 1 µg to 1 mg. In a preferred embodiment, the nasal aerosol device of the present invention provides a delivered dose of the active ingredient of at least 50 µg, more preferably at least 60 µg and most preferably at least 70 µg, while at the same time providing the desirable "soft spray".

The propellant of the pharmaceutical formulation of the present invention is preferably a hydrofluoroalkane (HFA) propellant, more preferably P134a (1,1,1,2-tetrafluoroethane), P227 (1,1,1,2,3,3,3-heptafluoropropane) or mixtures thereof. Other hydrofluorocarbons, hydrocarbons or aliphatic gases (e.g. butane or dimethylether) may be added to modify the propellant characteristics as required. However, it is preferred that P134a and/or P227 are the sole propellants present. The propellant preferably constitutes 80% to 99% w/w, more preferably 90 to 98% w/w, based on the total weight of the formulation.

The present invention is applicable to nasal spray devices for delivering all types of pharmaceutical formulations, but is particularly effective for delivering pharmaceutical formulations which include a co-solvent for the active ingredient. The co-solvent is generally present in order to solubilise the active ingredient and the precise nature of the co-solvent will therefore depend on the nature of the active ingredient. However, the co-solvent is preferably a $C_{2-6}$ aliphatic alcohol, such as ethanol or propylene glycol, and preferably ethanol. When required, the co-solvent is present in an amount sufficient to dissolve substantially all of the medicament present in the formulation and to maintain the medicament dissolved over the time period and conditions experienced by commercial aerosol products. Preferably the solvent is present in an amount to prevent precipitation of the active ingredient even at temperatures down to −20° C. The solvent is preferably anhydrous, although trace amounts of water absorbed by the ingredients, for example during manufacture of the medicament, may be tolerated. Anhydrous ethanol is particularly preferred. The co-solvent, preferably ethanol, is typically present at 1-20% w/w, more preferably 6-15% w/w and most preferably about 8% w/w, based on the total weight of the formulation.

In a specific embodiment of the present invention, the pharmaceutical formulation comprises beclomethasone dipropionate, ethanol and a propellant selected from 1,1,1,2-tetrafluoroethane (P134a), 1,1,1,2,3,3,3-heptafluoropropane (P227) and a mixture thereof. This formulation is typically used for the prophylaxis and/or treatment of seasonal allergic rhinitis (including hay fever) and perennial rhinitis. The active ingredient beclomethasone dipropionate is generally present in a formulation of the present invention in a therapeutically effective amount, i.e. an amount such that metered volumes of the medicament administered to the patient contains an amount of drug effective to exert the intended therapeutic action. The aerosol formulation preferably contains 0,02% to 0,8% w/w, more preferably 0.05% to 0.5% w/w of beclomethasone dipropionate, based on the total weight of the formulation.

A preferred formulation according to the present invention comprises 0.02% to 0.6% w/w beclomethasone dipropionate, 1% to 20% w/w ethanol and 80 to 99% w/w of propellant, wherein the percentages by weight are based on the total weight of the aerosol. A particularly preferred formulation consists essentially of beclomethasone dipropionate, ethanol and a propellant selected from 1,1,1,2-tetrafluoroethane, 1,1,1,2,3,3,3-heptafluoropropane and a mixture thereof; more preferably the formulation consists of these components.

The pharmaceutical formulation of the present invention is preferably substantially free of surfactant. Surfactants are often added to suspensions to stabilise the suspension. However, when the formulation of the present invention is a solution, a surfactant is not required. Nevertheless, small quantities can be tolerated without adversely affecting the formulation. Preferably the formulation contains no more than 0.0005% w/w of a surfactant based on the total weight of the formulation. Preferred formulations contain no surfactant. The presence of a significant amount of a surfactant is believed to be undesirable for solution formulations of beclomethasone dipropionate because surfactants such as oleic acid and lecithin are believed to promote chemical degradation of the active ingredient when the latter is dissolved in the mixture of the propellant and ethanol.

The pharmaceutical formulation of the present invention may be prepared by dissolving the desired amount of active ingredient in the desired amount of co-solvent accompanied by stirring or sonication. The aerosol canister may then be filled using conventional cold-fill or pressure-fill methods.

The present invention provides a nasal spray device for the delivery of a pharmaceutical formulation to the nasal cavity in metered doses. The device comprises a pressurised aerosol canister. Such canisters are known in the art and are commercially available. The aerosol canister 3 is typically composed of aluminium or an aluminium alloy. The internal surfaces of the aerosol canister 3 may be coated with a fluorocarbon polymer, such as PTFE or FEP, optionally together with non-fluorinated polymer to promote adhesion, such as PES. The canister includes a vial containing a pharmaceutical formulation comprising an active ingredient and a propellant. The aerosol canister further includes a metering valve having a valve stem axially displaceable relative to the vial to cause the dispensation of a metered dose of the pharmaceutical formulation through the valve stem. The device also comprises an actuator for the aerosol canister including a stem block having a receptacle into which the valve stem of the aerosol canister is received and axially located, and being displaceable relative to the vial of the aerosol canister to actuate the metering valve of the aerosol canister. The stem block further defines a discharge nozzle for the pharmaceutical formulation and a transfer channel through which a dispensed dose of the pharmaceutical formulation is able to pass from the valve stem to the discharge orifice. The actuator further comprises a delivery outlet, such as a nose piece, for the aerosol plume, the discharge orifice being arranged to direct the aerosol plume through the delivery outlet.

According to the present invention, the device is adapted to produce an aerosol plume for a dispensed dose of a formulation composition preferably having a spray force value no greater than 40 mN measured at a distance of 30 mm from the discharge orifice.

With reference to FIG. 1, a nasal spray device 1 according to the present invention is based on a conventional pressurised metered dose inhaler (pMDI), but modified for nasal use rather than for inhalation via the mouth. Accordingly, the device 1 comprises an actuator 2 accommodating an aerosol canister 3 containing a pharmaceutical formulation for delivery to the nasal cavity of a user.

The aerosol canister 3 is constructed to a standard design and specification and comprises a substantially cylindrical vial body 4 which contains the pharmaceutical formulation. The aerosol canister 3 is charged with a pharmaceutical formulation as described hereinabove. The vial body 4 is provided with a ferrule 5 which is crimped over a lip of the body to hermetically seal the pharmaceutical formulation under pressure.

Figure 2:
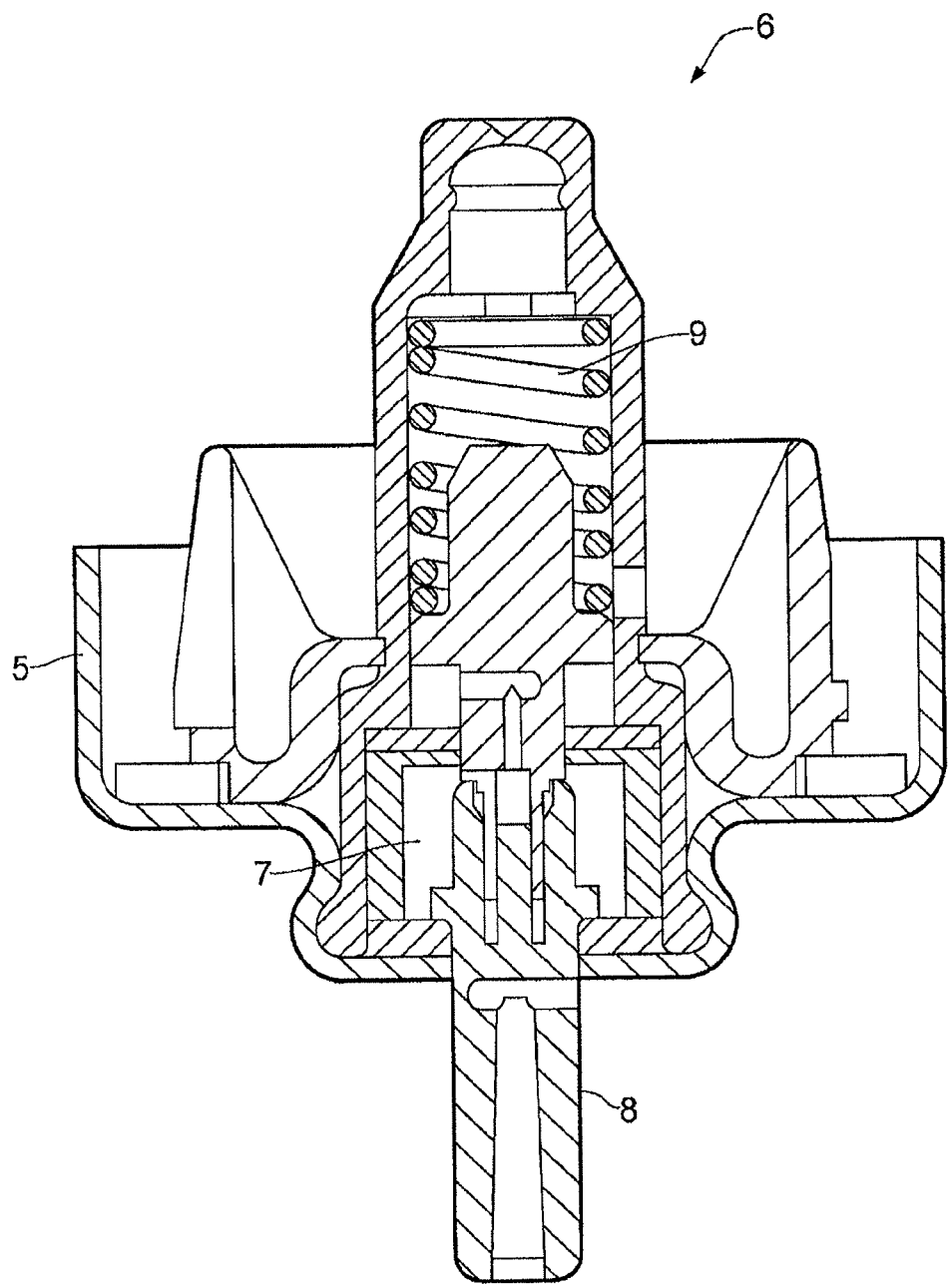
FIG. 2 shows a conventional valve for a pMDI.

The ferrule 5 of the aerosol canister 3 is provided with a metering valve 6 designed to deliver a metered amount of the pharmaceutical formulation to the user for each actuation of the valve 6. The metering valve 6 is of a known type available from manufacturers such as Consort Medical plc and 3M Drug Delivery Systems. See WO 99/47195 for further details of the metering valve suitable for use in the device of the present invention. The valve 6 generally comprises a metering chamber 7 (not visible in FIG. 1, but shown in FIG. 2 reproduced from WO 99/47195) and a valve stem 8 in the form of a narrow tube protruding outwardly from ferrule 5. The metering valve 6 is actuated by displacing the valve stem 8 into the valve body against the action of a valve spring 9 to allow the metered amount of the pharmaceutical formulation to vent from the metering chamber through the stem 8. The propellant component of the pharmaceutical formulation causes atomisation of the active ingredient by vaporising on release to the atmosphere. The metering chamber 7 is then recharged with the pharmaceutical formulation as the valve stem 8 is allowed to return to its starting position under the action of the valve spring 9.

With further reference to FIG. 1, the aerosol canister 3 is received into the open end of a body 10 of the actuator 2, with the valve stem 8 being received into and axially located by a stem block 11 of the actuator 2. The actuator body 10 is a moulded plastics component and the stem block 11 is formed as a protrusion which stands from the closed end of the actuator body 10. The stem block 11 includes a cylindrical receptacle configured for an interference fit with the valve stem 8 of the aerosol canister 3. The actuator body 10 generally defines a sleeve-like portion having a substantially circular cross-section, within which sleeve-like portion the aerosol canister 3 is axially displaceable relative to the stem block 11 and valve stem 8 to actuate the metering valve 6. A portion of the aerosol canister 3 at its non-valve end remains exposed in use so that the user is able to apply a manual pressure to displace the aerosol canister relative to the valve stem.

Although similar in the above-described respects, the nasal spray device 1 according to the present invention differs from conventional pMDIs in two important respects.

Firstly, the actuator body 10 defines a delivery outlet in the form of a nose piece 12 (rather than a mouth piece) for delivering the atomised pharmaceutical formulation to the nasal cavity. The delivery outlet may be a tubular nose piece adapted for insertion into the nostril, and a circular end of the nose piece may have an inner diameter of 5 to 7.5 mm, preferably about 7.2 mm. The delivery outlet, the delivery orifice and the transfer channel may be aligned with each other, that is to say they may have substantially identical axes. The axis of the delivery outlet may be substantially perpendicular, or at an angle of up to 20° to the perpendicular, to the aerosol canister and the receptacle of the stem block. Preferably an axis of the nose piece 12 defines an angle of about 80° with the sleeve-like portion of the actuator body 10. The nose piece 12 directly faces the stem block 11 so that an aerosol plume produced at the valve stem can be delivered through the nose piece 12 into the nasal cavity.

Secondly, the nasal spray device 1 according to the present invention differs from conventional pMDIs in relation to the design of the stem block 11. A stem block of a conventional pMDI is moulded with a discharge orifice facing the delivery outlet, and the discharge orifice is fluidly connected to the receptacle of the stem block so that the pharmaceutical formulation is able to pass from the aerosol canister out through the delivery outlet. By comparison, the nasal spray device 1 according to the present invention has a stem block 11 that is provided with a transfer channel 13 (not shown fully in FIG. 1) through which the pharmaceutical formulation is able to pass from the aerosol canister 3, through the nose piece 12, and into the nasal cavity of a user. In FIG. 1, the stem block 11 is shown having a first part 14 of the transfer channel 13 extending from a sump 15 underneath the receptacle of the stem block 11 into an opening defining a socket 16. The sump 15 is preferably rounded to help to prevent blockages. The socket 16 is adapted to receive a moulded plastic insert 17 which defines a second part 18 of the transfer channel 13 and the discharge orifice 19, as described hereinbelow in more detail (note that the insert 17 is not cut-away in FIG. 1). The first 14 and second 18 (in FIG. 3) parts together define a transfer channel 13 through which the pharmaceutical formulation is able to pass from the aerosol canister 3, through the nose piece 12, and into the nasal cavity of a user. That is, the transfer channel 13 has a first part 14 in fluid communication with the sump 15 of the stem block 11 and a second part 18 in fluid communication with the discharge orifice 19, the second part 18 and the discharge orifice 19 being defined by a separate insert received into an opening formed in the stem block of the actuator.

Figure 3:
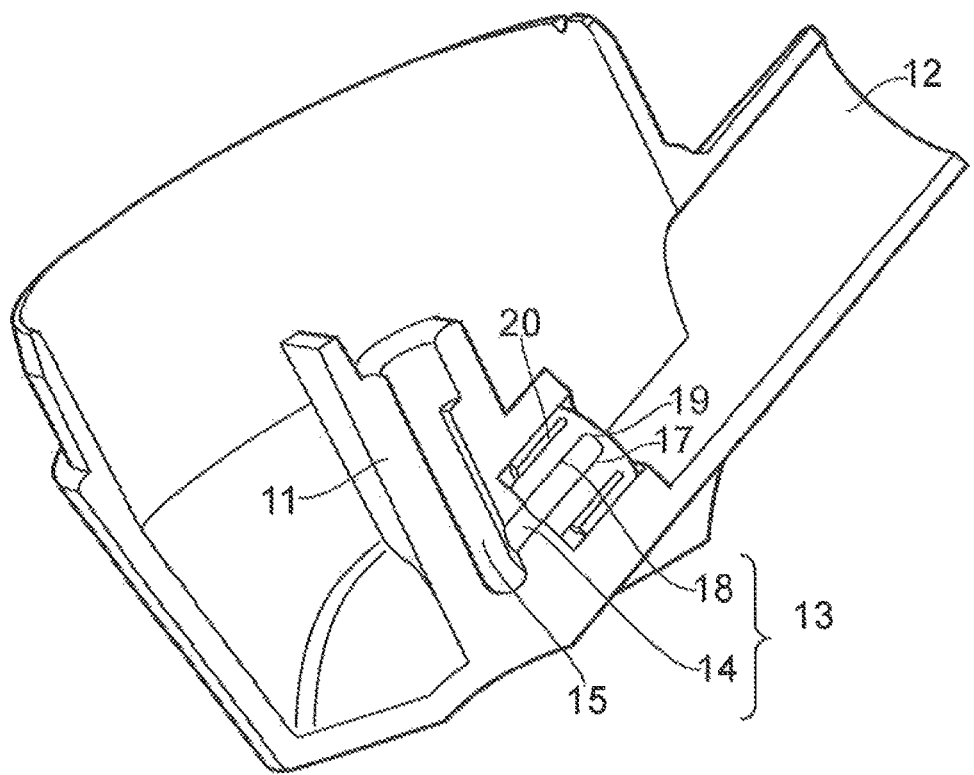
FIG. 3 shows another cut-away view showing a portion of the nasal spray device of FIG. 1 in greater detail.

FIG. 3 is a view similar to that of FIG. 1, but with the insert 17 cut-away to show the second part 18 of the transfer channel and the discharge orifice 19. It will also be seen more clearly that the sump 15 is narrower than the receptacle of the stem block 11 in order to locate axially the valve stem 8 of the aerosol canister (not shown in FIG. 3). An end of the insert 17 is provided with a radial flange from which a resilient sleeve 20 extends in a coaxial relationship with the second part 18 of the transfer channel 13 and discharge orifice 19. The resilient sleeve 20 provides an interference fit in the socket 16. Alternatively, or additionally, the insert 17 may be provided with a mechanical locking means for engagement with a corresponding means formed in the stem block, such as an annular flange (see flange 21 in FIG. 4) arranged to lock into a corresponding annular groove formed in the side wall of the socket 16.

The second part 18 of the transfer channel 13 and the discharge orifice 19 are shown as defined by a separate insert 17 received into an opening formed in the stem block 11 of the actuator 2. Such a configuration may provide a number of benefits. For example, a nasal spray device can then be configured simply by altering the design of the insert. Furthermore, the insert may be manufactured with smaller tolerances than those of other components of the nasal spray device. In this way, it may be possible to reduce unit-to-unit variation in the delivered dose and spray force value of the device. However, the device of the present invention is not limited to a separate insert and the first 14 and second parts 18 of the transfer channel 13 may be integrally formed into a unitary structure. Such a unitary structure may be produced by injection moulding.

The transfer channel 13 preferably has circular cross-section. It also preferably tapers down towards the discharge orifice 19. The transfer channel 13 may taper down towards the discharge orifice end, for example such that a side wall of the chamber defines an angle of 0.5 to 3°, preferably about 1°. It is believed that the risk of blockages may be reduced by tapering the chamber in this way. The risk of blockages may also be reduced by avoiding sharp corners in the fluid path. A further preferred feature is a maximum transverse dimension of 1.0 to 3.0 mm, preferably from 1.2 to 2 mm and most preferably about 1.5 mm. The transfer channel 13 has a length of 3 to 20 mm, more preferably 4 mm to 15 mm, more preferably 4 to 10 mm and most preferably about 7 mm. The transfer channel 13 serves as an expansion chamber for modifying the spray characteristics of the aerosol plume, in particular by reducing the spray force value for the plume, as compared to the plume generated using a device with no expansion chamber.

The discharge orifice 19 has a diameter of 0.15 to 0.65 mm, preferably 0.20 to 0.50 mm and most preferably about 0.4 mm. It is believed that discharge orifices smaller than 0.15 mm may be prone to blockages. A length of the outlet orifice, measured between the outlet end of the transfer channel 13 and the opening of the outlet orifice, (also known as the "land length") is 0.5 to 1.0 mm, preferably 0.6 to 0.9 mm and most preferably about 0.65 mm. The length of the outlet orifice is believed to be significant because it may strongly influence the shape (spread) of the aerosol plume. A focused plume is important in ensuring that a large proportion of the dose is delivered to the nasal cavity of the user and not retained on the surfaces of the actuator 2.

Figure 4:
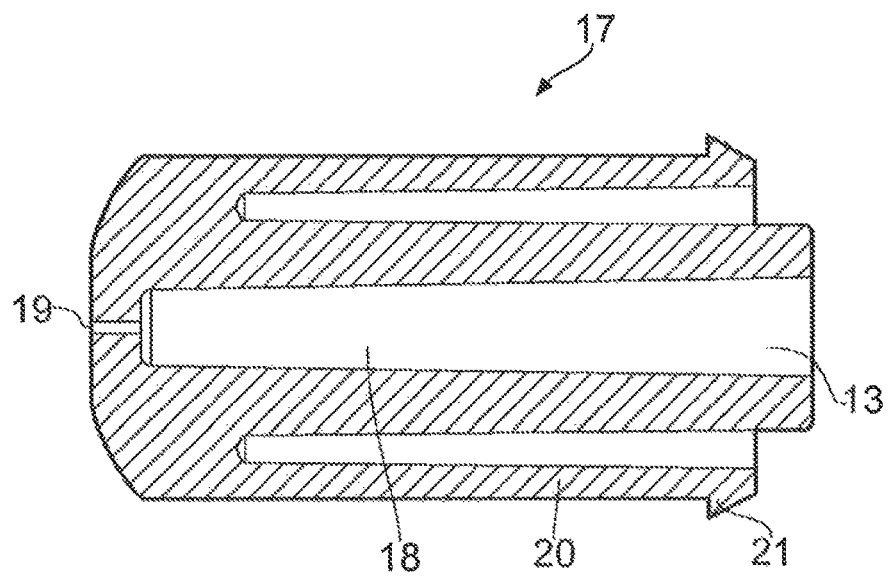
FIG. 4 is a cross-sectional view showing a component for the nasal spray device shown in FIGS. 1 and 3.
Figure 5:
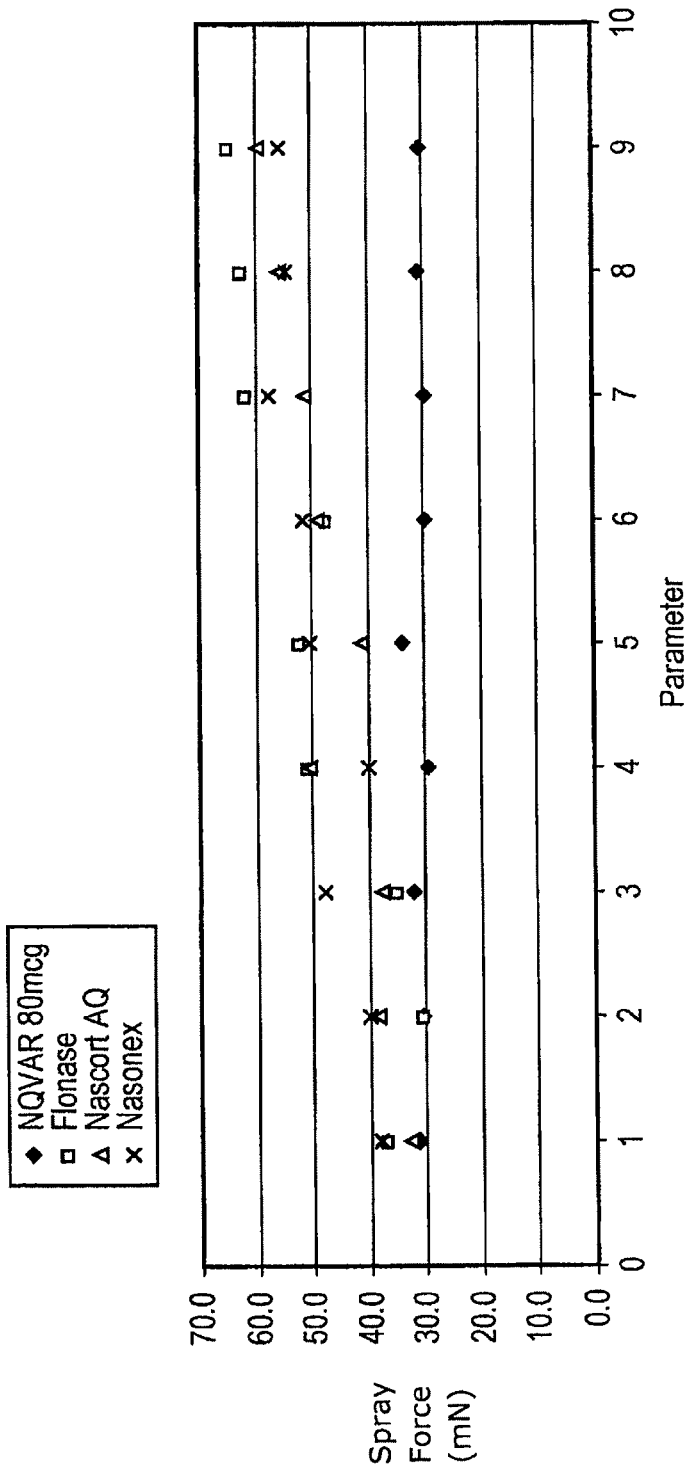
FIG. 5 is a chart showing the effect of actuation variables on the spray force values for four different nasal spray devices.

FIG. 4 is a cross-sectional view showing an insert 17 suitable for use with the nasal spray device shown in FIGS. 1 and 3. Like reference numerals indicate the same or corresponding elements. The length of the insert 17 not only affects the volume of the transfer channel 13, but also modifies the distance of the delivery outlet 12 from the discharge orifice 19. It is believed that a greater proportion of the dose is delivered to the nasal cavity of the user when this distance is reduced (for example, by employing a longer insert).

Before use of the nasal spray device 1 described hereinabove, the user shakes the device 1 several times, as is normal practice for pMDIs. To use the device 1, the user inserts the nose piece 12 into a nostril and depresses the exposed end of the aerosol canister 3. Displacement of the canister 3 relative to the valve stem 8 causes actuation of the metering valve 6 and a metered amount of the pharmaceutical formulation is vented from the metering chamber in the aerosol canister 3. The formulation passes through the sump 15 and into the transfer channel 13 where it undergoes controlled expansion, before finally being discharged through the discharge orifice 19 and the nose piece 12.

As described hereinabove, the present invention provides a nasal spray device in which the conventionally unpleasant effects of using a propellant-based formulations are avoided by providing the device with soft spray characteristics; by which is meant a spray force value of no greater than 40 mN measured at 30 mm from the discharge orifice 19. The minimum spray force is less critical and may be any positive non-zero value. Preferably the spray force is 10 to 40 mN measured at 30 mm from the discharge orifice 19. It has been found that such soft sprays are well tolerated by users and allows pMDI technology to be applied to the nasal delivery of medicaments, thereby avoiding the disadvantages associated with pump-action devices.

The desired spray force value may be achieved by appropriate combination of the orifice diameter, land length and the geometry of the transfer channel as described hereinabove. In particular, a lower spray force value is favoured by a smaller orifice diameter. However, a longer land length and a geometry of the transfer channel such that the transverse dimension tapers down towards the discharge orifice is also preferred. Moreover, a balance must be obtained in order to prevent deposition of the active ingredient on the internal surfaces of the device which in turn can lead to reduced dose uniformity and even clogging of the device. In a preferred embodiment, the discharge orifice has a diameter of 0.16 to 0.65 mm and a length of 0.5 to 1.0 mm, and the transfer channel has a transverse dimension which tapers down towards the discharge orifice end.

It has further been found that the proportion of the dose of active ingredient that is retained by the device described herein may be no greater than 40%, preferably no greater than 30% and more preferably no greater than 20%. It has been found that the delivered dose uniformity of the device may be acceptable, with a relative standard deviation (RSD) no greater than 20%, preferably no greater than 10%.

The spray force value is given as the value measured at a predetermined distance, typically 30 mm, from the discharge orifice 19. Spray force values may be measured using conventional techniques, such as with an impaction plate coupled to a digital load cell, e.g. a Copley SFT 1000 spray force tester available from Copley Scientific Limited, Nottingham, United Kingdom. This device comprises a circular impaction plate coupled to a digital load mail for measuring forces acting on the impaction plate. The device includes a movable carriage to which a spray device is mounted so that its spray outlet is centred on and faces the impaction plate. The spray device is then actuated and the load cell measures the spray force value of the spray.

Spray force values are measured under controlled conditions of temperature of 25° C., pressure of 101 kPa and relative humidity of 50%. The impaction plate is mounted in a vertical orientation. The spray device is mounted in the movable carriage so that the discharge orifice of the device is positioned 30 mm from the impaction plate. The spray device is then actuated and the maximum compression force of the impaction plate recorded. Six actuations are measured for each device to be tested. The mean of these six values is recorded as the spray force value for the device. The measurements are preferably taken using an actuation velocity of 70 mm/s and an acceleration of 7,000 $mm/s^2$, although this is not critical as the spray force is not significantly affected by these variables.

EXAMPLES

Example 1

Spray force values for a nasal spray device according to the present invention were measured using a variety of actuation velocities and accelerations. The device tested was of the type shown in FIGS. 1 and 3 and configured with a nose piece having an inner diameter of 8.2 mm. The stem block insert had the shape generally shown in FIG. 4. The orifice size is 0.4 mm and insert length is 10 mm. The device was loaded with a HFA aerosol canister configured to provide an 80 μg dose (ex-valve) of beclomethasone dipropionate. The solution formulation consisted of the beclomethasone dipropionate as the active ingredient, together with ethanol 4.8 mg per actuation as a co-solvent and P134a 55.1 mg per actuation as a propellant. Spray force values for three commercially available manual pump-type nasal spray devices were also measured using the same variety of actuation velocities and accelerations for comparison purposes. Details of the devices tested are summarised in Table 1.

TABLE 1

| Devices | | | | |
|---|---|---|---|---|
| Device | Product name | Dose size, ex-actuator (μg) | API | Manufacturer |
| Example 1 | — | 80 | Beclomethasone dipropionate (solution) | — |
| Comparative Example 1 | FLONASE ® | 50 | Fluticasone propionate (suspension) | GlaxoSmithKline |
| Comparative Example 2 | NASACORT AQ ® | 55 | Triamcinolone acetonide (suspension) | Sanofi-Aventis |
| Comparative Example 3 | NASONEX ® | 50 | Momethasone furoate monohydrate (suspension) | Schering-Plough |

The testing was carried out using a Copley SFT 1000 spray force tester available from Copley Scientific Limited, Nottingham, United Kingdom following the test procedure described hereinabove. The nasal spray device according to the present invention (Example 1) was actuated for the tests using a SPRAYVIEW® Vereo MDx Automated Actuation System available from Proveris Scientific Corporation, Marlborough, Mass., USA. The manual pump-type nasal spray devices (Comparative Examples 1 to 3) were actuated using a SPRAYVIEW® Vereo NSx Automated Actuation System available from Proveris Scientific Corporation, Marlborough, Mass., USA.

The actuation velocities and accelerations used for the testing, together with the results of the testing, are set out in Table 2. The results are also illustrated in FIG. 5, which is a chart plotting spray force values (vertical axis) against actuation settings. It will be seen from the chart that spray force values for the manual pump-type nasal spray devices vary significantly with the actuation parameters, but this is not the case for the nasal spray device according to the invention (NQVAR 80 μg in FIG. 5).

TABLE 2

Spray force values

| Actuation parameters | | | Spray force value (mN) | | |
|---|---|---|---|---|---|
| velocity (mm/s) | acceleration (mm/s$^2$) | Example 1 | Comparative Example 1 | Comparative Example 2 | Comparative Example 3 |
| 60 | 6000 | 31.4 | 36.8 | 32.9 | 38.1 |
| 60 | 7000 | 30.5 | 30.6 | 38.2 | 39.9 |
| 60 | 8000 | 32.1 | 35.1 | 37.7 | 47.8 |
| 70 | 6000 | 29.3 | 50.7 | 50.3 | 39.8 |
| 70 | 7000 | 33.8 | 52.2 | 40.9 | 50.5 |
| 70 | 8000 | 29.9 | 47.4 | 48.9 | 51.4 |
| 80 | 6000 | 29.9 | 61.8 | 51.3 | 57.6 |
| 80 | 7000 | 30.8 | 62.3 | 55.8 | 54.6 |
| 80 | 8000 | 30.3 | 64.9 | 59.6 | 55.8 |

Statistical analysis was performed on the results for all four devices tested to look for significant sources of variation in the spray force value data. The following equation was used to conduct ANOVA (Analysis of Variance):

$$y_{ijk} = \mu + \tau_i + v_j + \alpha_k + (v\alpha)_{jk} + (\tau v)_{ij} + (\tau\alpha)_{jk} + (\tau v\alpha)_{ijk} + \varepsilon_{ijk} \quad \text{(equation 1)}$$

where $\mu$ is the overall mean, $y_{ijk}$ is the spray force value for the i$^{th}$ device, j$^{th}$ velocity and k$^{th}$ acceleration, $\tau_i$ is the i$^{th}$ device, $v_j$ is the j$^{th}$ level of velocity, $\alpha_k$ is the k$^{th}$ level of acceleration, $v\alpha_{jk}$ is the interaction of velocity and acceleration, $\tau v_{ij}$ is the interaction of device and velocity, $\tau\alpha_{ik}$ is the interaction of device and acceleration, $\tau v\alpha_{ijk}$ is the interaction of device, velocity and acceleration, and $\varepsilon$ is the error term.

The ANOVA yielded values of F for each source of possible variation. The F values and associated p-values are recorded in Table 3.

TABLE 3

Statistical analysis for all devices tested

| Source | F | p-value | Significant? |
|---|---|---|---|
| Device | 71.73 | <0.0001 | Yes |
| Velocity | 75.89 | <0.0001 | Yes |
| Acceleration | 2.26 | 0.1074 | No |
| Velocity*Acceleration | 0.30 | 0.8806 | No |
| Device*Velocity | 12.83 | <0.0001 | Yes |
| Device*Acceleration | 1.04 | 0.4032 | No |
| Device*Velocity*Acceleration | 1.67 | 0.0758 | No |

It will be seen from Table 3 that the spray force value data is significantly affected by the particular device being used, the velocity of actuation, and the interaction of the device and the velocity of actuation. Subsequently, reduced ANOVA for the manual pump-type nasal spray devices only (Comparative Examples 1 to 3) was conducted. The following equation was used:

$$y_{ijk} = \mu + \tau_i + v_j + \alpha_k + (v\alpha)_{jk} + \varepsilon_{ijk} \quad \text{(equation 2)}$$

where $\mu$ is the overall mean, $\tau_i$ is the i$^{th}$ device, $v_j$ is the j$^{th}$ level of velocity, $\alpha_k$ is the k$^{th}$ level of acceleration, $v\alpha_{jk}$ is the interaction of velocity and acceleration, and $\varepsilon$ is the error term.

The F values and associated p-values are recorded in Table 4.

TABLE 4

Statistical analysis for manual pump-type nasal spray devices

| Source | F | p-value | Significant? |
|---|---|---|---|
| Device | 1.56 | 0.2127 | No |
| Velocity | 73.41 | <0.0001 | Yes |
| Acceleration | 2.05 | 0.1323 | No |
| Velocity*Acceleration | 0.10 | 0.9811 | No |

It will be seen from Table 4 that velocity of actuation is a significant source of variation for spray force values of manual pump-type nasal spray devices. Reduced ANOVA was also conducted for the nasal spray device according to the present invention (Example 1). The following equation was used:

$$y_{ijk} = \mu + v_j + \alpha_k + (v\alpha)_{jk} + \varepsilon_{jk} \quad \text{(equation 3)}$$

where $\mu$ is the overall mean, $v_j$ is the j$^{th}$ level of velocity, $\alpha_k$ is the k$^{th}$ level of acceleration, $v\alpha_{jk}$ is the interaction of velocity and acceleration, and $\varepsilon$ is the error term.

The F values and associated p-values are recorded in Table 5.

TABLE 5

Statistical analysis for nasal spray device according to the present invention

| Source | F | p-value | Significant? |
|---|---|---|---|
| Velocity | 0.43 | 0.6541 | No |
| Acceleration | 0.96 | 0.3903 | No |
| Velocity*Acceleration | 1.40 | 0.2500 | No |

It will be seen from Table 5 that none of velocity of actuation, acceleration of actuation and the interaction between velocity and acceleration of actuation are considered to be significant sources of variation for spray force values. Accordingly, the nasal spray device according to the present invention provides the advantage of consistent spray force values, regardless of the velocity and/or acceleration of actuation. This advantage is particularly important in relation to use by the very young and the elderly, who may find it difficult to actuate the device repeatedly with a consistent velocity.

Examples 2-5

Further testing was carried out on the test devices of the type shown in FIGS. 1 and 3 having different stem block inserts. The devices were each configured with a nose piece having an inner diameter of 7.2 mm. The stem block insert of each device had the shape generally shown in FIG. 4, with the dimensions provided in Table 6. The orifice size is 0.4 mm, the insert length of 10 mm, a land length of 0.65 mm, and a tip diameter of 6.4 mm. The device was loaded with an HFA aerosol canister configured to provide a 100 µg dose (ex-valve) of beclomethasone dipropionate. The solution formulation consisted of the beclomethasone dipropionate as the active ingredient, together with ethanol 4.8 mg per actuation as a co-solvent and P134a 55.1 mg per actuation as a propellant.

TABLE 6

| | Devices | |
|---|---|---|
| Example no. | Discharge orifice diameter (mm) | Insert length (mm) |
| Example 2 | 0.22 | 5 |
| Example 3 | 0.22 | 10 |
| Example 4 | 0.4 | 5 |
| Example 5 | 0.4 | 10 |
| Comparative Example 4 | 0.7 | 5 |
| Comparative Example 5 | 0.7 | 10 |

The nasal spray devices were tested for spray force values using the test procedure set out hereinabove. The results of the testing are set out in Table 7.

TABLE 7

| | Spray force values and RSD. | |
|---|---|---|
| Example no. | Spray force value (mN) | RSD (%) |
| Example 2 | 8.7 | 13 |
| Example 3 | 10.8 | 19 |
| Example 4 | 29.8 | 6 |
| Example 5 | 34.1 | 6 |
| Comparative Example 4 | 51.4 | 13 |
| Comparative Example 5 | 53.3 | 13 |

It will be seen that all four examples provided spray force values no greater than 40 mN. The two comparative examples provided spray force values in excess of this figure, and are therefore outside the scope of the present invention. In all cases the relative standard deviation (RSD) was less than 20%. It will be appreciated that the spray force value for a nasal spray device according to the present invention depends to a large degree on the size and shape of the stem block insert. In general, for any given dose size, lower spray force values may be obtained with smaller orifice diameters and with shorter insert lengths.

The nasal spray devices were also tested for spray content uniformity (SCU) to measure variation in delivered doses of the active ingredient. The results of this hosting are set out in Table 8.

TABLE 8

| | Delivered doses | | | | | |
|---|---|---|---|---|---|---|
| | Ex. 1 | Ex. 2 | Ex. 3 | Ex. 4 | Comp. Ex. 1 | Comp Ex. 2 |
| Delivered dose through valve (µg) | 123.5 | 103.8 | 109.8 | 100.6 | 106.5 | 101.5 |
| RSD (%) | 8 | 12 | 10 | 6 | 8 | 6 |
| Delivered dose through actuator (µg) | 79.1 | 80.9 | 73.1 | 77.9 | 71.5 | 78.7 |
| RSD (%) | 9 | 9 | 14 | 4 | 8 | 6 |
| Retained in actuator (%) | 36 | 22 | 34 | 22 | 33 | 22 |

It will be seen that all of the tested examples and comparative examples provided a delivered dose through the actuator of at least 70 µg, with an acceptable relative standard deviation (RSD). Furthermore, in all cases, less than 40% of the dose delivered through the valve was retained on the surfaces of the actuator. Examples 2 and 4, for which the insert length was 10 mm, exhibited markedly reduced retention of the dose in the actuator.

What is claimed:

1. A nasal spray device for the delivery of a pharmaceutical formulation to a nasal cavity in metered doses, the nasal spray device comprising:
a pressurised aerosol canister including a vial containing a pharmaceutical formulation comprising an active ingredient, and a propellant, the aerosol canister further including a metering valve having a valve stem; and
an actuator for the aerosol canister, the actuator including a stem block having a receptacle into which the valve stem of the metering valve of the aerosol canister is received and axially located, the valve stem being displaceable relative to the vial of the aerosol canister to actuate the metering valve of the aerosol canister, a sump extending below the receptacle, the stem block further defining a cylindrical discharge orifice for the pharmaceutical formulation and a transfer channel through which a dispensed dose of the pharmaceutical formulation is able to pass from the sump to the cylindrical discharge orifice,
wherein the actuator further comprises a delivery outlet for an aerosol plume, the cylindrical discharge orifice being arranged to direct the aerosol plume through the delivery outlet,
wherein the nasal spray device is adapted to produce an aerosol plume for a dispensed dose having a spray force value no greater than 40 millinewtons (mN) measured at a distance of 30 millimeters (mm) from the cylindrical discharge orifice, wherein the cylindrical discharge orifice has a diameter of 0.15 to 0.65 mm and a length of 0.6 mm to 1.0 mm, and wherein the transfer channel has a length of 3 to 20 mm and has a transverse dimension in a range of 1.2 mm to 2 mm, the transverse dimension being measured at its maximum extent.

2. The nasal spray device of claim 1, wherein the transfer channel has a circular cross-section.

3. The nasal spray device of claim 1, wherein the transfer channel has a transverse dimension which tapers down towards an end of the cylindrical discharge orifice.

4. The nasal spray device of claim 1, wherein the transfer channel has a first part in fluid communication with the sump of the stem block and a second part in fluid communication with the cylindrical discharge orifice, the second part and the cylindrical discharge orifice being defined by a separate insert received into an opening formed in the stem block of the actuator.

5. The nasal spray device of claim 4, wherein an end of the insert is provided with a radial flange from which a resilient sleeve extends in a coaxial relationship with the second part of the transfer channel and the discharge orifice.

6. The nasal spray device of claim 5, wherein the resilient sleeve provides an interference fit in the opening and/or the insert is provided with a mechanical locking means for engagement with a corresponding means formed in the stem block.

7. The nasal spray device of claim 6, wherein the mechanical locking means comprises an annular flange and the corresponding means comprises a corresponding annular groove formed in a side wall of the opening, the annular flange being arranged to lock into the annular groove.

8. The nasal spray device of claim 1, wherein the pharmaceutical formulation further comprises a co-solvent present at 0.5 to 20% percentage by weight (w/w), based on a total weight of the pharmaceutical formulation.

9. The nasal spray device of claim 8, wherein the active ingredient is beclomethasone dipropionate, the propellant is selected from P134a, P227 or mixtures thereof, or other pressurised gases, and the co-solvent is anhydrous ethanol.

10. The nasal spray device of claim 8, wherein the co-solvent is ethanol or propylene glycol.

11. The nasal spray device of claim 8, wherein the co-solvent is present at 6 to 15% w/w based on a total weight of the pharmaceutical formulation.

12. A method of delivering a pharmaceutical formulation comprising:
spraying metered doses of the pharmaceutical formulation into the nasal cavity via the nasal spray device of claim 1.

13. The nasal spray device of claim 1, wherein the pharmaceutical formulation is a solution formulation.

14. The nasal spray device of claim 1, wherein the pharmaceutical formulation is a suspension formulation.

15. The nasal spray device of claim 1, wherein the delivery outlet is a tubular nose piece adapted for insertion into a nostril.

16. The nasal spray device of claim 15, wherein the tubular nose piece has an inner diameter of 5 to 7.5 mm.

17. The nasal spray device of claim 1, wherein the discharge orifice has a diameter of 0.20 to 0.50 mm.

18. The nasal spray device of claim 1, wherein the discharge orifice has a diameter of 0.4 mm.

19. The nasal spray device of claim 1, wherein the transverse dimension of the transfer channel is 1.5 mm.

20. The nasal spray device of claim 1, wherein the transfer channel has a length of 4 mm to 15 mm.

21. The nasal spray device of claim 1, wherein the transfer channel has a length of 4 mm to 10 mm.

22. The nasal spray device of claim 1, wherein the delivery outlet, the discharge orifice and the transfer channel are aligned with each other.

23. The nasal spray device of claim 1, wherein the active ingredient is a steroid selected from beclomethasone dipropionate, budesonide, fluticasone propionate and mometasone furoate.

24. The nasal spray device of claim 1, wherein the active ingredient is beclomethasone dipropionate.

25. The nasal spray device of claim 1, wherein a delivered dose of the active ingredient of at least 50 µg is provided.

26. The nasal spray device of claim 1, wherein the propellant is P134a and/or P227.

27. The nasal spray device of claim 1, wherein the propellant constitutes 80% w/w to 99% w/w based on a total weight of the pharmaceutical formulation.

28. The nasal spray device of claim 1, wherein the formulation comprises 0.02% to 0.6% w/w beclomethasone dipropionate, 1% to 20% w/w ethanol and 80% to 99% w/w of propellant, wherein the percentages by weight are based on the total weight of the aerosol.

29. The nasal spray device of claim 1, wherein the discharge orifice has a diameter of 0.22 or 0.4 mm and a length of 0.65 mm, wherein the transfer channel has a length of 5 or 10 mm, and wherein the pharmaceutical formulation comprises beclomethasone dipropionate as active ingredient, P134a as propellant and ethanol as co-solvent.

30. The nasal spray device of claim 1, wherein the discharge orifice has a diameter of 0.4 mm, wherein the transfer channel has a length of 10 mm, wherein the delivery outlet has an inner diameter of 8.2 mm, and wherein the pharmaceutical formulation comprises beclomethasone dipropionate as active ingredient, P134a as propellant and ethanol as co-solvent.

* * * * *